(12) United States Patent
Romero et al.

(10) Patent No.: US 7,446,094 B2
(45) Date of Patent: Nov. 4, 2008

(54) CYTOTOXIC DEPSIPEPTIDES

(75) Inventors: Paco Romero, Leon (ES); Leyre Malet, Leon (ES); Librada Maria Cañedo, Leon (ES); Carmen Cuevas, Madrid (ES); José Fernando Reyes, Tres Cantos (ES)

(73) Assignee: Instituto Biomar S.A., Madrid (ES)

( * ) Notice: Subject to any disclaimer, the term of this patent is extended or adjusted under 35 U.S.C. 154(b) by 95 days.

(21) Appl. No.: 10/562,079

(22) PCT Filed: Jun. 23, 2004

(86) PCT No.: PCT/GB2004/002694

§ 371 (c)(1),
(2), (4) Date: Dec. 22, 2005

(87) PCT Pub. No.: WO2005/000880

PCT Pub. Date: Jan. 6, 2005

(65) Prior Publication Data

US 2007/0082878 A1 Apr. 12, 2007
US 2008/0227765 A9 Sep. 18, 2008

(30) Foreign Application Priority Data

Jun. 24, 2003 (GB) .................................. 0314726.1

(51) Int. Cl.
*A61K 38/15* (2006.01)
*C07K 11/00* (2006.01)

(52) U.S. Cl. .......................... 514/11; 435/71.3; 514/9; 530/323; 530/331; 530/333; 530/825

(58) Field of Classification Search ........................ None
See application file for complete search history.

(56) References Cited

FOREIGN PATENT DOCUMENTS

JP 11-180997 7/1999

OTHER PUBLICATIONS

Akaji et al., "Convergent Synthesis of (-)-Mirabazole C Using a Chloroimidazolidium Coupling Reagent, CIP", J. Org. Chem, 61, pp. 3350-3357, 1996.

Kanoh et al., "Mechercharmycins A and B, Cytotoxic Substances from Marine-derived Thermoactinomyces sp. YM3-251", J. Antibiot., 58 (4), 2005, pp. 289-292.

Knight et al., "Synthesis of the Tris-oxazole Ring System of Ulapualides", Synlett Letters, Jan. 1990, pp. 36-37.

Liu et al., "Studies Directed Toward the Total Synthesis of Kabiramide C: Asymmetric Synthesis of the C7-C19 Fragment", Tetrahedron Letters, 39, 1998, pp. 6143-6146.

Panel et al., Studies Directed Toward the Synthesis of Ulapualide A. Asymmetric Synthesis of the C8-C25 Tris-Oxazole Fragment, J. Org. Chem., 61, 1996, pp. 6496-6497.

G. Pattenden, "Synthesis Studies with Natural Oxazoles and Thiazoles", J. Heterocyclic Chem., 29, 1992, pp. 607-618.

Wipf et al., "Total Synthesis of (-)-Thiangazole and Structurally Related Polyazoles", J. Org. Chem., 60, 1995, pp. 7224-7229.

Wipf et al., "A New Synthesis of Highly Funtionalized Oxazoles", J. Org. Chem., 58, 1993, pp. 3604-3606.

*Primary Examiner*—Jeffrey E Russel
(74) *Attorney, Agent, or Firm*—Fish & Richardson P.C.

(57) ABSTRACT

Compounds of general formula (I) wherein $R_1$, $R_2$, $R_3$ are as defined and $R_4$ groups are each independently selected from $NR_2$, O and S; are of use in treatment of cancers.

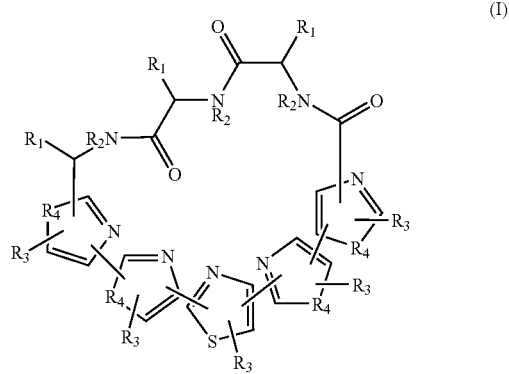

13 Claims, 9 Drawing Sheets

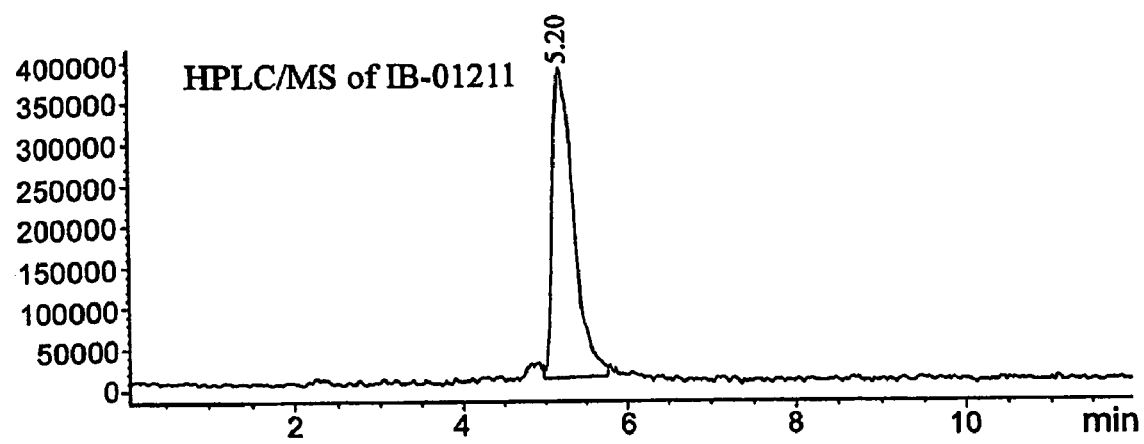
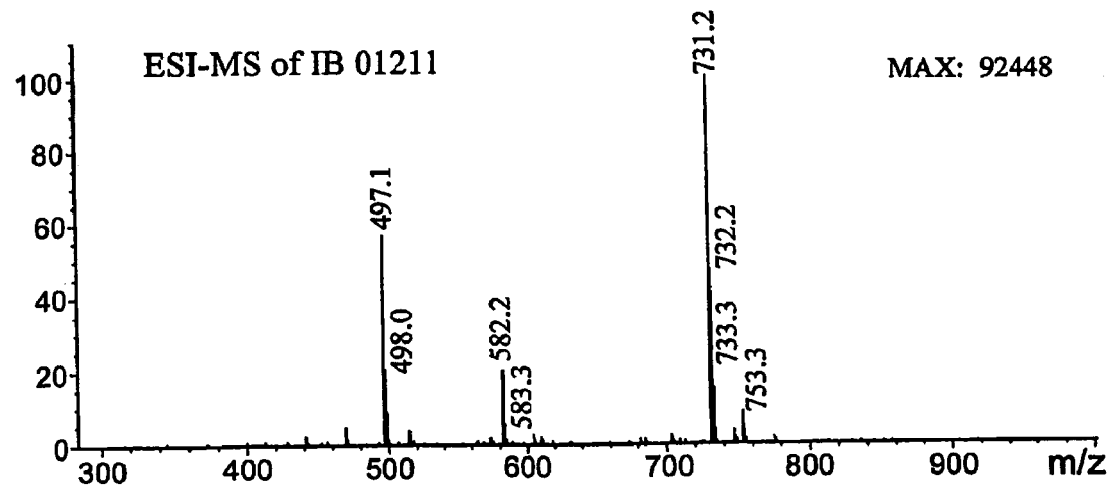
Fig.9

```
                    SEQUENCE LISTING

<160> NUMBER OF SEQ ID NOS: 1

<210> SEQ ID NO 1
<211> LENGTH: 1329
<212> TYPE: DNA
<213> ORGANISM: Marine sponge
<220> FEATURE:
<221> NAME/KEY: misc_feature
<222> LOCATION: 175
<223> OTHER INFORMATION: n = a, t, c or g

<400> SEQUENCE: 1
gcggacgggt gagtaacgcg tgggcaacct gcctgcaaga tcgggataac cccgggaaac     60
cggagctaat accgataat  ctttatcctc gcatgggag  gaagtaaaag aaggtttcgg    120
ccttcacttg cagatgggcc cgcggcgcat tagctagttg gtgaggtaga ggctnaccaa    180
ggcgacgatg cgtagccgac ctgagagggt gatcggccac actgggactg agacacggcc    240
cagactccta cgggaggcag cagtagggaa ttttccgcaa tgggcgaaag cctgacggag    300
caacgccgcg tgagtgagga cggttttcgg attgtaaagc tctgtccttt cggaagaaca    360
gcaaggagag gaaatgctcc ttgtgtgacg gtacgaaaga agaaagcccc ggctaactac    420
gtgccagcag ccgcggtaat acgtaggggg caagcgttgt ccggaattat tgggcgtaaa    480
gcgcgcgcag gcggcctgtt aagtcggatg tgaaaggcca cggctcaacc gtggagcggc    540
atccgaaact ggcgggcttg agtgcagaag aggagagtga aattcccggt gtagcggtgg    600
aatgcgtaga gatcgggagg aacaccagtg gcgaaggcgg ctctctggtc tgcaactgac    660
gctgaggcgc gaaagcgtgg ggagcgaaca ggattagata ccctggtagt ccacgccgta    720
aacgatgagt gctaggtgtt gggggtgtca tgccctctgt gccgaaggaa acccaataag    780
cactccgcct ggggagtacg gccgcaaggc tgaaactcaa aggaattgac gggggcccgc    840
acaagcggtg gagcatgtgg tttaattcga agcaacgcga agaaccttac cagggcttga    900
catccttctg atcgcttgag agatcaagct tctcttcgga gcagaagtga caggtggtgc    960
atggttgtcg tcagctcgtg tcgtgagatg ttgggttaag tcccgcaacg agcgcaaccc   1020
ttatggttag ttgccagcat taagttgggc actctaacga gacagccggt gaaagccgga   1080
```

-continued

```
ggaaggtggg gatgacgtca aatcatcatg cccttatgt cctgggccac acacgtgcta  1140
caatggctgg tacaacgggt agcgaagctg cgaagtgtag ccaatcccaa aaaaccagtc  1200
tcagttcgga tcgtaggctg caactcgcct acgtgaagct ggaatcgcta gtaatcgcgg  1260
atcagcatgc cgcggtgaat acgttcccgg gccttgtaca caccgcccgt cacaccacga  1320
gagtttgca                                                         1329
```

CYTOTOXIC DEPSIPEPTIDES

This application is the National Stage of PCT/GB2004/002694, filed on Jun. 23, 2004, which claims the benefit of GB 0314726.1, filed on Jun. 24, 2003. The contents of these two applications are incorporated herein by reference in their entireties.

FIELD OF THE INVENTION

The present invention relates to new depsipeptide compounds, pharmaceutical compositions containing them and their use as antitumoural agents.

BACKGROUND OF THE INVENTION

Several cyclic peptides obtained from marine organisms have been disclosed (see for example Rudi A. et al., *J. Nat. Prod.*, 2003, 66, 575-577: "Didmolamide A and B, two new cyclic hexapeptides from the marine Ascidian Didemnum molle").

JP 11180997 discloses an antitumour compound of formula

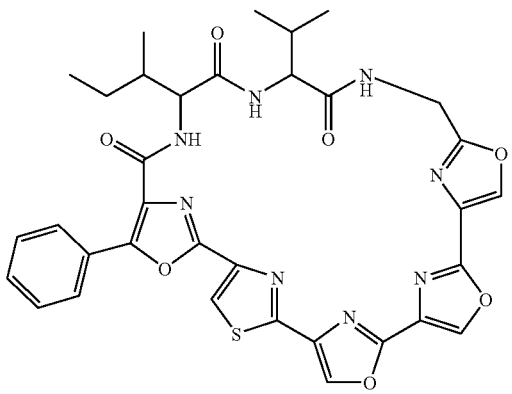

which is obtained from *Streptomyces nobilis*. Its $IC_{50}$ in Hela S3 cells is 14 nM.

Cancer is a leading cause of death in animals and humans. Several efforts have been and are still being undertaken in order to obtain an antitumour agent active and safe to be administered to patients suffering from a cancer. The problem to be solved by the present invention is to provide compounds that are useful in the treatment of cancer.

SUMMARY OF THE INVENTION

The present invention is directed to compounds of general formula I or pharmaceutically acceptable salts, derivatives, prodrugs or stereoisomers thereof:

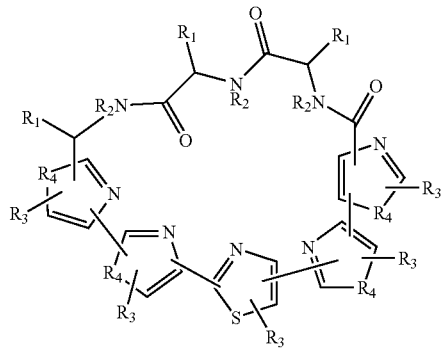

(I)

wherein
$R_1$ groups are each independently selected from the group consisting of hydrogen, halogen, cyano, hydroxyl, nitro, azido, substituted or unsubstituted alkyl, substituted or unsubstituted alkylidene, substituted or unsubstituted alkenyl, substituted or unsubstituted alkynyl, substituted or unsubstituted alkoxy, substituted or unsubstituted aryl, substituted or unsubstituted heterocyclic group and substituted or unsubstituted acyl;

$R_3$ groups are each independently selected from the group consisting of hydrogen, halogen, cyano, hydroxyl, nitro, azido, substituted or unsubstituted alkyl, substituted or unsubstituted alkenyl, substituted or unsubstituted alkynyl, substituted or unsubstituted alkoxy, substituted or unsubstituted aryl, substituted or unsubstituted heterocyclic group and substituted or unsubstituted acyl;

$R_4$ groups are each independently selected from $NR_2$, O and S; and $R_2$ groups are each independently selected from the group consisting of hydrogen, substituted or unsubstituted alkyl, substituted or unsubstituted aryl, substituted or unsubstituted alkoxy and substituted or unsubstituted acyl.

The present invention also relates to the obtaining of the compounds of formula I, including the compound we call IB-01211 which is of formula:

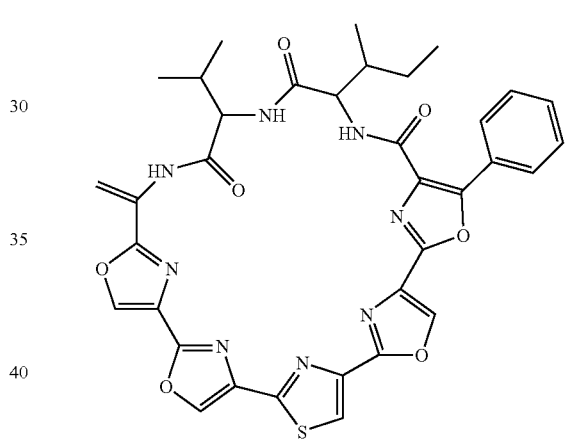

IB-01211 can be obtained from a strain of microorganism capable of producing it. The preferred process comprises the steps of cultivating a strain of microorganisms capable of producing IB-01211 in an aqueous nutrient medium with assimilable carbon and nitrogen sources and salts, under controlled submerged aerobic conditions, and then recovering and purifying the compound from the cultured broth.

Other compounds of this invention can be derived from IB-01211, or can be made by synthesis. Thus, the oxazole/thiazole/imidazole fragment of the compounds of the present invention can be synthesised by using the teaching of the following literature: Panek J. S. et al. "Studies directed toward the synthesis of Ulapualide A. Asymmetric Synthesis of the C8-C25 tris-oxazole fragment" *J. Org. Chem.* 1996, 61, 6496-6497; Panek J. S. et al. "Studies directed toward the total synthesis of kabiramide C: asymmetric synthesis of the C7-C19 fragment" *Tetrahedron Lett.* 1998, 39, 6143-6146; Panek J. S. et al. "Synthesis of the fully functionalized tris-oxazole fragment found in metabolites derived from marine organisms" *Tetrahedron Lett.* 1997, 38, 5445-5448; Pattenden G. "Synthetic studies with natural oxazoles and thiazoles" *J. Heterocyclic Chem.* 1992, 29, 607-618; Pattenden G. et al. "Synthesis of the tris-oxazole ring system of ulapualides" *Synlett.* 1990, 36-37; Kiso Y. et al. "Convergent synthesis of (–)-mirabazole C using a chloroimidazolidium coupling reagent, CIP" *J. Org. Chem.* 1996, 61, 3350-3357; Wipf P. et al. "Total synthesis of (–)-thiangazole and structurally related polyazoles" *J. Org. Chem.* 1995, 60, 7224-7229; Wipf P. et al. "A new synthesis of highly functionalised oxazoles" *J. Org. Chem.* 1993, 58, 3604-3606. Once the oxazole/thiazole/imidazole fragment is synthesised the aminoacidic fragment is introduced by using conventional methods of peptide synthesis already known by the skilled person in the art.

Thus, compounds of formula I including IB-01211 can be made by coupling of the following components:

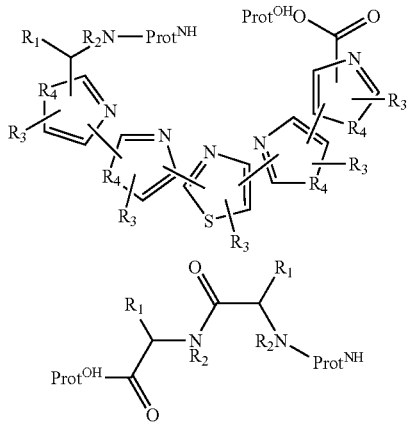

where $R_1$, $R_2$, $R_3$, $R_4$ are as defined, $Prot^{OH}$ is an optional protecting group for hydroxy, and $Prot_{NH}$ is an optional protecting group for amino. As appropriate, the respective protecting groups can be replaced by other reactive groups to encourage the desired coupling, which typically takes place sequentially first to join the oxazole/thiazole/imidazole fragment to one end of the amino acidic fragement, and then to close the ring.

In another aspect, the present invention is directed to pharmaceutical compositions containing a compound of formula I or pharmaceutically acceptable salts, derivatives, prodrugs or stereoisomers thereof, together with a pharmaceutically acceptable carrier or diluent.

In another aspect, the present invention is also directed to the use of compounds of formula I or pharmaceutically acceptable salts, derivatives, prodrugs or stereoisomers thereof in the treatment of cancer, or in the preparation of a medicament for the treatment of cancer.

BRIEF DESCRIPTION OF THE DRAWINGS

FIG. 9. HPLC/MS chromatogram and ESI-MS spectrum of purified IB-01211

DETAILED DESCRIPTION OF THE INVENTION

Figure 1:
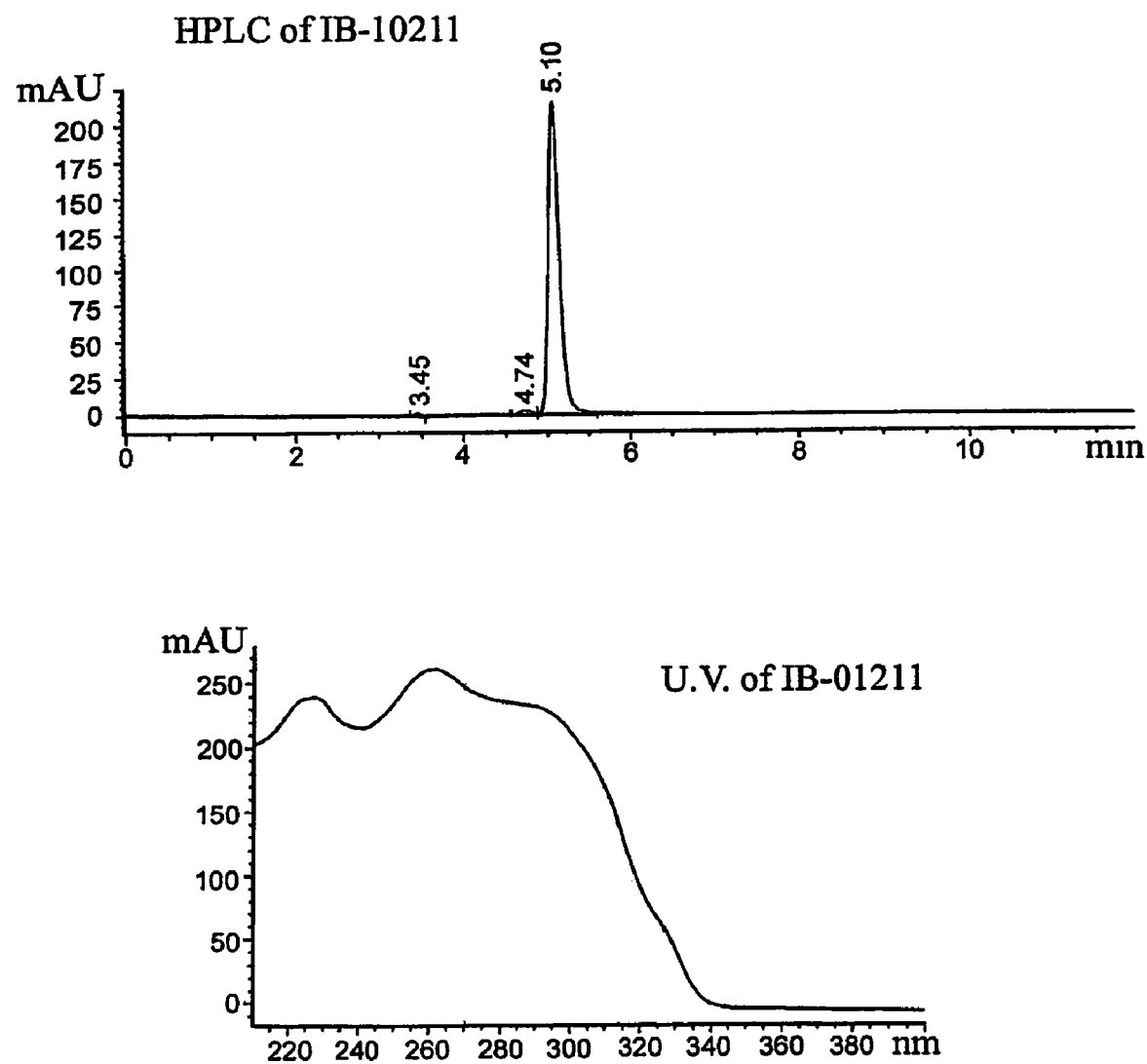
FIG. 1. HPLC/UV chromatogram and UV spectrum of purified IB-01211

The present invention relates to compounds of general formula I as defined above.

In these compounds the substituents can be selected in accordance with the following guidance:

Alkyl and alkoxy groups preferably have from 1 to 12 carbon atoms. One more preferred class of alkyl groups has 1 to about 8 carbon atoms, yet more preferably 1 to about 6 carbon atoms, and most preferably 1, 2, 3 or 4 carbon atoms. Methyl, ethyl, propyl including isopropyl, and butyl including isobutyl, sec-butyl and terc-butyl are particularly preferred alkyl groups in the compounds of the present invention. As used herein, the term alkyl, unless otherwise modified, refers to both cyclic and noncyclic groups, although cyclic groups will comprise at least three carbon ring members.

Alkylidene groups may be branched or unbranched and preferably have from 1 to 12 carbon atoms. One more preferred class of alkylidene groups has from 1 to about 8 carbon atoms, yet more preferably from 1 to about 6 carbon atoms, and most preferably 1, 2, 3 or 4 carbon atoms. Methylidene, ethylidene and propylidene including isopropylidene are particularly preferred alkylidene groups in the compounds of the present invention.

Preferred alkenyl and alkynyl groups in the compounds of the present invention have one or more unsaturated linkages and from 2 to about 12 carbon atoms, more preferably 2 to about 8 carbon atoms, still more prefereably 2 to about 6 carbon atoms, even more prefereably 1, 2, 3 or 4 carbon atoms. The terms alkenyl and alkynyl as used herein refere to both cyclic and noncyclic groups, although straight or branched noncyclic groups are generally more preferred. In a general sense, we include alkylidene within alkenyl, they both being substituents with a double bond.

Suitable aryl groups in the compounds of the present invention include single and multiple ring compounds, including multiple ring compounds that contain separate and/or fused aryl groups. Typical aryl groups contain from 1 to 3 separated or fused rings and from 6 to about 18 carbon ring atoms. Specifically preferred aryl groups include substituted or unsubstituted phenyl, naphthyl, biphenyl, phenanthryl and anthracyl.

Suitable acyl groups include alkanoyl groups which have from 2 to about 12 carbon atoms, more preferably from 2 to about 8 carbon atoms, still more preferably from 2 to about 6 carbon atoms, even more preferably 2 carbon atoms. Other acyl groups include alkenylacyl, alkynylacyl, arylacyl, heterocyclylacyl.

Suitable heterocyclic groups include heteroaromatic and heteroalicyclic groups. Suitable heteroaromatic groups in the compounds of the present invention contain one, two or three heteroatoms selected from N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, imidazolyl, indolyl, benzofuranyl and benzothiazol. Suitable heteroalicyclic groups in the compounds of the present invention contain one, two or three heteroatoms selected from N, O or S atoms and include, e.g., tetrahydrofuranyl, tetrahydropyranyl, piperidinyl, morpholino and pyrrolindinyl groups.

The groups above mentioned may be substituted at one or more available positions by one or more suitable groups such as OR', SR', SOR', $SO_2R'$, $NO_2$, NHR', N(R')$_2$, NHCOR', N(COR')$_2$, NHSO$_2$R', CN, halogen, C(=O)R', CO$_2$R', OC(=O)R' wherein each of the R' groups is independently selected from the group consisting of H, OH, NO$_2$, NH$_2$, SH, CN, halogen, C(=O)H, C(=O)alkyl, CO$_2$H, substituted or unsubstituted $C_1$-$C_{18}$ alkyl, substituted or unsubstituted $C_2$-$C_{18}$ alkenyl, substituted or unsubstituted $C_2$-$C_{18}$ alkynyl and substituted or unsubstituted aryl.

Suitable halogen substituents in the compounds of the present invention include F, Cl, Br and I.

The term "pharmaceutically acceptable salts, derivatives, prodrugs" refers to any pharmaceutically acceptable salt, ester, solvate, hydrate or any other compound which, upon administration to the patient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art.

For instance, pharmaceutically acceptable salts of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartate, malate, mandelate, methanesulphonate and p-toluenesulphonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

The compounds of the invention may be in crystalline form either as free compounds or as solvates (e.g. hydrates) and it is intended that both forms are within the scope of the present invention. Methods of solvation are generally known within the art.

Any compound that is a prodrug of a compound of formula I is within the scope and spirit of the invention. The term "prodrug" is used in its broadest sense and encompasses those derivatives that are converted in vivo to the compounds of the invention. Such derivatives would readily occur to those skilled in the art, and include, for example, compounds where a free hydroxy group is converted into an ester derivative.

The compounds of the present invention represented by the above described formula I may include enantiomers depending on their asymmetry or diastereoisomers. The single isomers and mixtures of the isomers fall within the scope of the present invention.

Preferred compounds of the invention are those of general formula

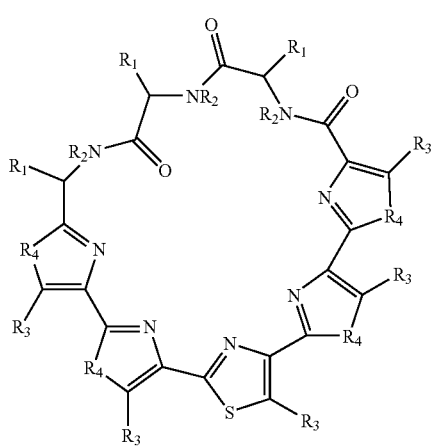

(II)

wherein $R_1$, $R_2$, $R_3$ and $R_4$ groups have the same meaning as defined above.

Preferred $R_1$ groups are substituted or unsubstituted alkyl and substituted or unsubstituted alkylidene, more preferred are substituted or unsubstituted $C_1$-$C_6$ alkyl and substituted or unsubstituted $C_1$-$C_6$ alkylidene, still more preferred are isopropyl, sec-butyl and methylene. Preferred $R_2$ groups are H and substituted or unsubstituted alkyl, and more preferred is H. Preferred $R_3$ groups are H and substituted or unsubstituted aryl, and more preferred are H and phenyl. Preferred $R_4$ group is O.

One particularly preferred compound of formula I is compound IB-01211:

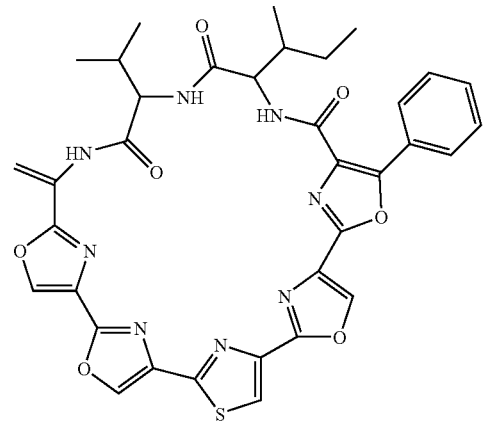

The preferred stereochemistry of the above mentioned compound is the following

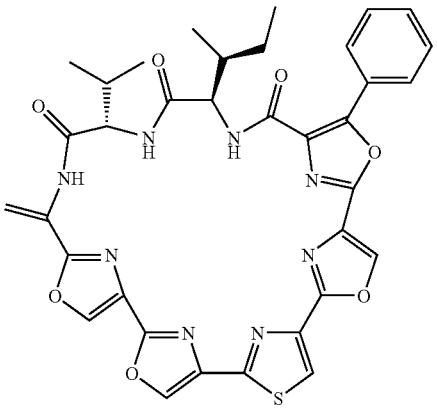

Compound IB-01211 is preferably obtained from an actinomycete, named strain ES7-008. A culture of this strain has been deposited in the Colección Española de Cultivos Tipo at the University of Valencia, in Spain, under the accession number CECT 3358. This deposit has been made under the provisions of the Budapest Treaty.

The microorganism strain ES7-008 is phylogenetically close to *Thermoactinomyces* genus. The organism was isolated from an unidentified marine sponge. The taxonomic methods were as follows.

1. Colonial morphology:
    ISP Media No 2, 4, 5 and 6: Shirling B. E., and D. Gotlieb. *Int. J. Syst. Bactenol.* 16:313, 1966
    ATCC Medium No 172: American Type Culture Catalog 17th edition, 1989. Rockville, Md. U.S.A.
    Czapek Agar Difco
    Bennet Agar, Waksman, S. A *The Actinomycetes* vol.II: 331, 1961
    All media were supplemented with 50% ASW 2. Physiological characteristics:
   ISP medium n° 1, Shirling and Gotlieb.
   NaCl resistance: ATCC 172 with 0, 2, 4, 5, 7 and 10% NaCl.
   Carbon utilization: ISP-9, Shirling and Gotlieb.
3. Fatty acids analysis,
   Shirling B. E., and D. Gotlieb. *Int. J. Syst Bacteriol.* 16:313, 1966
4. Whole cell sugar analysis:
   Guerrant G. O., and C. W. Moss. *Anal. Chem.* 56:633, 1984
5. Diaminopinelic acids analysis:
   Hasegaw T., M. Takizawa, and S. Tanida, J. Gen. Appl. Microbiol. 29:319, 1983
   All cultures were incubated at 28° C. and records of results were made weekly up to 21 days.
   A description of the organism is as follows:

Morphology:
After 21 days at 28° C. growth was observed in ISP2 and 172 broth supplemented with artificial sea water (ASW). No aerial mycelium was formed. Substrate mycelium was branched. Spores are formed both in solid and liquid media as endospores.

Physiology:
No diffusible pigments were formed by strain ES7-008, neither on solid or liquid media. The optimum of NaCl concentration in the medium for optimal growth was in the 4%-7% range. Growth did not occur at 28° C. in the absence of salt even in rich media compositions as ATCC's 172 medium. The optimum growth temperature range was between 28° C.-40° C.
The strain ES7-008 can utilize glucose, melibiose, xylose, and ethanol as carbon sources. Growth was poor on fructose, sucrose, rhamnose, and galactose. The organism did not grow on arabinose, mannose or myo-inositol.

Chemical Composition:

Aminoacids:
meso-2,6-diaminopimelic acid was present in the whole hydrolysated cell of strain ES7-008

Fatty Acids Composition:
The mayor fatty acids were identified as i-15:0, a-15:0, 15:0, i-16:0, i-17:1, i-17:0, and a-17:0. The fatty acids composition of strain ES7-008 and other actinomycete strains is in the following table, where the composition is given as percentage of total fatty acids content.

|  | 13:0 | i-14:0 | 14:0 | i-15:0 | a-15:0 | 15:0 | i-16:1 | i-16:0 |
|---|---|---|---|---|---|---|---|---|
| ES7-008 | <1 | <1 | <1 | <1 | 64.2 | 6.29 | 1.36 | <1 |
| STALBUS | <1 | 6.52 | <1 | 9.88 | 22.92 | <1 | 5.50 | 25.29 |
| SPAMETH | 1.21 | 10.34 | <1 | 1.86 | <1 | 4.30 | <1 | 15.51 |
| SPVIRIDO | <1 | 4.04 | 1.10 | 18.94 | 2.71 | 4.89 | <1 | 26.44 |
| AMCITRE | <1 | <1 | 3.18 | <1 | <1 | 1.03 | <1 | 6.37 |
| APBRAZIL | <1 | 3.15 | <1 | 15.46 | 18.91 | 2.76 | <1 | 19.07 |
| AMPDIGIT | <1 | 11.57 | <1 | 11.21 | 9.96 | <1 | 2.87 | 34.23 |
| AMYORIE | <1 | 3.40 | 2.37 | 19.94 | 4.66 | 1.17 | <1 | 11.85 |
| MNCHALC | <1 | 1.68 | <1 | 8.91 | 2.29 | 1.53 | 1.15 | 38.23 |
| MNECHCA | <1 | 1.17 | <1 | 6.97 | 1.24 | 2.81 | <1 | 30.88 |
| MNFUSCA | <1 | <1 | <1 | 26.56 | 6.53 | <1 | <1 | 8.58 |
| SACCAER | <1 | 3.06 | 1.35 | 14.41 | 8.62 | 1.04 | 5.68 | 20.07 |
| NOAFRI | 1.51 | 5.43 | 3.35 | 4.62 | <1 | 7.46 | 3.09 | 22.18 |
| MTSALMO | <1 | 1.12 | 1.28 | 6.75 | <1 | 7.83 | 7.53 | 21.58 |
| MTRUBRA | <1 | 1.40 | 1.38 | 4.12 | <1 | 3.41 | 7.27 | 25.00 |
| MTROSEO | 2.03 | 3.65 | 5.14 | 3.86 | <1 | 9.03 | 3.02 | 12.31 |
| AMROSEO | <1 | 2.19 | 1.24 | 6.73 | 1.09 | 6.94 | 1.43 | 22.21 |
| MTFERRU | 1.03 | 1.91 | 1.19 | 1.94 | <1 | 6.43 | 4.12 | 21.50 |

-continued

|  | 16:1 | 16:0 | i-17:1 | i-17:0 | a-17:0 | 17:1 | 17:0 |
|---|---|---|---|---|---|---|---|
| ES7-008 | 4.52 | <1 | <1 | 14.68 | 4.14 | 1.45 | <1 |
| STALBUS | <1 | 3.75 | 1.28 | 3.38 | 8.60 | <1 | <1 |
| SPAMETH | 5.63 | 8.62 | 1.08 | <1 | <1 | 24.02 | 9.43 |
| SPVIRIDO | <1 | 4.43 | <1 | 2.60 | 1.58 | 11.36 | 8.58 |
| AMCITRE | 12.62 | 40 | <1 | <1 | <1 | <1 | 1.16 |
| APBRAZIL | 2.15 | 1.79 | <1 | 2.39 | 9.64 | 11.18 | 2.82 |
| AMPDIGIT | <1 | 1.08 | <1 | 1.28 | 5.08 | 4.39 | 1.64 |
| AMYORIE | 5.59 | 18.41 | <1 | 2.99 | 4.44 | 3.09 | 2.73 |
| MNCHALC | <1 | 1.88 | 1.49 | 2.32 | 2.25 | 5.43 | 6.95 |
| MNECHCA | <1 | 2.29 | 1.63 | 4.11 | 1.68 | 12.15 | 4.90 |
| MNFUSCA | <1 | <1 | 7.30 | 11.89 | 13.25 | 2.90 | 3.37 |
| SACCAER | 13.84 | 6.16 | 4.55 | 2.20 | 5.31 | 2.02 | <1 |
| NOAFRI | 2.69 | 5.15 | 2.35 | <1 | <1 | 8.15 | 4.75 |
| MTSALMO | 1.21 | 1.97 | 1.01 | <1 | 1.07 | 11.58 | 5.53 |
| MTRUBRA | 2.63 | 3.89 | 2.17 | 1.08 | <1 | 6.84 | 4.97 |
| MTROSEO | 3.46 | 6.95 | 1.17 | <1 | <1 | 13.51 | 4.46 |
| AMROSEO | 2.21 | 3.61 | 2.74 | 1.03 | <1 | 10.97 | 4.33 |
| MTFERRU | 2.32 | 2.34 | <1 | <1 | <1 | 23.51 | 5.71 |

|  | i-18:1 | i-18:0 | cis-18:1 | 18:0 |
|---|---|---|---|---|
| ES7-008 | <1 | <1 | <1 | <1 |
| STALBUS | <1 | 1.09 | <1 | <1 |
| SPAMETH | 7.11 | <1 | 4.60 | 1.04 |
| SPVIRIDO | 7.48 | <1 | <1 | 1.16 |
| AMCITRE | <1 | <1 | 14.25 | 2.82 |
| APBRAZIL | <1 | <1 | 3.38 | 1.06 |
| AMPDIGIT | <1 | 1.76 | 7.60 | 1.54 |
| AMYORIE | <1 | <1 | 6.21 | 3.04 |
| MNCHALC | 14.58 | 1.31 | 1.28 | 2.68 |
| MNECHCA | 7.23 | <1 | 10.05 | 1.69 |
| MNFUSCA | 3.59 | <1 | 2.33 | 1.94 |
| SACCAER | <1 | <1 | <1 | 1.43 |
| NOAFRI | 17.03 | <1 | <1 | 1.23 |
| MTSALMO | 17.34 | <1 | <1 | <1 |
| MTRUBRA | 15.44 | 1.25 | <1 | 1.61 |
| MTROSEO | 18.67 | <1 | 1.77 | <1 |
| AMROSEO | 17.84 | <1 | <1 | <1 |
| MTFERRU | 12.15 | 1.27 | 1.43 | <1 |

ES7-008 = strain ES25-008;
AMCITRE = *Actinomadura citrea* DSM 43461;
AMPDIGIT = *Ampullariella digitata* ATCC 15349;
AMROSEO = *Actinomadura roseoviolacea* DSM 43144;
AMYORIE = *Amycolatopsis orientalis* DSM 40040;
APBRAZIL = *Actinoplanes braziliensis* ATCC 25844;
MNCHALC = *Micromonospora chalcea* ATCC 31395;
MNECHCA = *Micromonospora echinospora calichinensis* NRRL 15839;
MNFUSCA = *Micromonospora fusca* NRRL B-3298;
MTFERRU = *Microtetraspora ferruginea* DSM 43553;
MTROSEO = *Microtetraspora roseola* ATCC 33579;
MTRUBRA = *Microtetraspora rubra* ATCC 27031;
MTSALMO = *Microtetraspora salmonea* ATCC 33580;
NOAFRI = *Nocardiopsis africana* DSM 43748;
SACCAER = *Saccharothrix aerocolonigenes* NRRL B-3298;
SPAMETH = *Streptosporangium amethystogenes* DSM 43179;
SPVIRIDO = *Streptosporangium viridogriseum* ATCC 25242;
STALBUS = *Streptomyces albus* DSM 40313

Sugar:
The whole cell sugar pattern did not show a specific profile

Phylogenetic Analysis:
Partial sequence of 16S rDNA was performed following standard procedures. The DNA of the organism was extracted after homogenization under liquid nitrogen. The 16S rDNA gene was amplified by the polymerase chain reaction using the eubacterial primers 27f and 1492r. The partial sequences were obtained using the primers 357r, 926r, and 1492r. All the primers used in this work were described by Lane, D.J.

*Nucleic acid techniques in bacterial systematics:* 115, 1991. The partial sequence obtained (SEQ ID NO: 1) was:

GCGGACGGGTGAGTAACGCGTGGGCAACCTGCCTGCAAGATCGGGATAAC

CCCGGGAAACCGGAGCTAATACCGAATAATCTTTATCCTCGCATGGGAG

GAAGTAAAAGAAGGTTTCGGCCTTCACTTGCAGATGGGCCCGCGGCGCAT

TAGCTAGTTGGTGAGGTAGAGGCTNACCAAGGCGACGATGCGTAGCCGAC

CTGAGAGGGTGATCGGCCACACTGGGACTGAGACACGGCCCAGACTCCTA

CGGGAGGCAGCAGTAGGGAATTTTCCGCAATGGGCGAAAGCCTGACGGAG

CAACGCCGCGTGAGTGAGGACGGTTTTCGGATTGTAAAGCTCTGTCCTTT

CGGAAGAACAGCAAGGAGAGGAAATGCTCCTTGTGTGACGGTACGAAAGA

AGAAAGCCCCGGCTAACTACGTGCCAGCAGCCGCGGTAATACGTAGGGGG

CAAGCGTTGTCCGGAATTATTGGGCGTAAAGCGCGCGCAGGCGGCCTGTT

AAGTCGGATGTGAAAGGCCACGGCTCAACCGTGGAGCGGCATCCGAAACT

GGCGGGCTTGAGTGCAGAAGAGGAGAGTGGAATTCCCGGTGTAGCGGTGG

AATGCGTAGAGATCGGGAGGAACACCAGTGGCGAAGGCGGCTCTCTGGTC

TGCAACTGACGCTGAGGCGCGAAAGCGTGGGGAGCGAACAGGATTAGATA

CCCTGGTAGTCCACGCCGTAAACGATGAGTGCTAGGTGTTGGGGGTGTCA

TGCCCTCTGTGCCGAAGGAAACCCAATAAGCACTCCGCCTGGGGAGTACG

GCCGCAAGGCTGAAACTCAAAGGAATTGACGGGGGCCCGCACAAGCGGTG

GAGCATGTGGTTTAATTCGAAGCAACGCGAAGAACCTTACCAGGGCTTGA

CATCCTTCTGATCGCTTGAGAGATCAAGCTTCTCTTCGGAGCAGAAGTGA

CAGGTGGTGCATGGTTGTCGTCAGCTCGTGTCGTGAGATGTTGGGTTAAG

TCCCGCAACGAGCGCAACCCTTATGGTTAGTTGCCAGCATTAAGTTGGGC

ACTCTAACGAGACAGCCGGTGAAAGCCGGAGGAAGGTGGGGATGACGTCA

AATCATCATGCCCCTTATGTCCTGGGCCACACACGTGCTACAATGGCTGG

TACAACGGGTAGCGAAGCTGCGAAGTGTAGCCAATCCCAAAAAACCAGTC

TCAGTTCGGATCGTAGGCTGCAACTCGCCTACGTGAAGCTGGAATCGCTA

GTAATCGCGGATCAGCATGCCGCGGTGAATACGTTCCCGGGCCTTGTACA

CACCGCCCGTCACACCACGAGAGTTTGCA

This sequence was confronted with the Gene Bank depositary using the Blastn algorithm. The phylogenetic studies were performed using the Phylip package developed by Felsenstein, J. *Cladistics* 5:164, 1989. A consensus phylogenetic tree was constructed after bootstrapping the sample. Strain ES7-008 was grouped with the *Thermoactinomyces* group. A differentiating trait of strain ES7-008 with *Thermoactinomyces* is a lack of aerial mycelium and the need of salt for growth.

Fermentation:

ES7-008 produces compound IB-01211 when it is cultured under controlled conditions in a suitable medium. This strain is preferably grown in an aqueous nutrient medium, under aerobic and mesophilic conditions, preferably at 28° C.-40° C. and at a pH ranging between 6.0 and 8.0. A wide variety of liquid culture media can be used for the cultivation of the organism. Useful media are those that include an assimilable carbon source, such as starch, dextrin, sugar molasses, glucose, an assimilable nitrogen source such as protein, hydrolysed protein, defatted meals, corn steep, and useful inorganic anions and cations such a sodium, magnesium, potassium, ammonium, sulfate, chloride, phosphate, carbonate. Trace elements may be added also. Aeration is preferably achieved by supplying air to the fermentation medium. Agitation is provided by a mechanical impeller. Conventional fermentation tanks have been found to be well suited for carrying out the cultivation of this organism. The addition of nutrients and pH control as well as antifoaming agents during the different stages of fermentation may be needed for increasing production and avoiding foaming.

Compound IB-01211 can be produced starting with a frozen lyophilized mycelium of ES7-008. A mycelial mass is obtained by culturing the initial cells in shake flasks with a culture medium containing some of the ingredients described above at mesophilic temperatures and in aerobic conditions. This step may be repeated several times as needed and the material collected will be used as an inoculum to seed one or several fermentation tanks with the appropriate culture medium. If it is desired these tanks can be used for developing the inoculum or for the production stage, depending on the broth volume needed. Sometimes the production medium may be different than the ones used for inoculum development. Typical media are disclosed that can be used for inoculum development and for production of IB-01211 are in the following table.

| Inoculum medium | | Production medium | |
|---|---|---|---|
| Soybean flour | 5 g | Yeast | 5 g |
| Glucose | 1 g | Peptone | 1 g |
| Starch | 24 g | Soybean flour | 3 g |
| Beef extract | 3 g | Soybean meal | 15 g |
| Yeast extract | 5 g | Yeast extract | 5 g |
| Tryptone | 5 g | Tryptone | 2 g |
| $CaCO_3$ | 4 g | $CaCO_3$ | 4 g |
| NaCl | 5 g | NaCl | 4 g |
| $Na_2SO_4$ | 7 g | $Na_2SO_4$ | 1 g |
| KCl | 0.2 g | KCl | 0.5 g |
| $MgCl_2$ | 2 g | $MgCl_2$ | 2 g |
| $H_2O$ | To 1 liter | $K_2HPO_4$ | 0.5 g |
| | | $H_2O$ | To 1 liter |

Production of IB-01211 can be monitored by whole broth assay against murine leukemia P-388 or by HPLC.

Compound IB-01211 can be isolated from the mycelial cake by extraction with a suitable mixture of solvents such as $CHCl_3:CH_3OH:H_2O$. The activity is concentrated in the lower layer. The extracts from two repeated extraction can be combined and evaporated to dryness in vacuo.

Separation and purification of IB-01211 from the crude active extract can be performed using the proper combination of conventional chromatographic techniques.

Fractionation can be guided by the antitumour activity of fractions, by TLC visualized with vanillin in concentrated $H_2SO_4$ or by analytical HPLC with photodiode-array and MS detector. HPLC analysis is performed at room temperature using an analytical column Symmetry C18 (5μ) and a MeOH:$H_2O$:HOAc 95:5:1 mobile phase at a flow rate of 0.3 ml/min and plotted at 260 nm. In this conditions the IB-01211 retention time is 5.1 min as it is shown in FIG. 9.

An important feature of the above described compounds is their bioactivity and in particular their cytotoxic activity. With this invention we provide novel pharmaceutical compositions of these compounds that possess cytotoxic activity, and their use as antitumour agents. Thus the present invention further provides pharmaceutical compositions comprising a compound of this invention or a pharmaceutically acceptable salt, derivative, prodrug or stereoisomer thereof with a pharmaceutically acceptable carrier.

Examples of pharmaceutical compositions include any solid (tablets, pills, capsules, granules, etc.) or liquid (solutions, suspensions or emulsions) suitable composition for oral, topical or parenteral administration.

Pharmaceutical compositions containing compounds of the invention may be delivered by liposome or nanosphere encapsulation, in sustained release formulations or by other standard delivery means.

Administration of the compounds or compositions of the present invention may be by any suitable method, such as intravenous infusion, oral preparations, intraperitoneal and intravenous administration. We prefer that infusion times of up to 24 hours are used, more preferably 1-12 hours, with 2-6 hours most preferred. Short infusion times which allow treatment to be carried out without an overnight stay in hospital are especially desirable. However, infusion may be 12 to 24 hours or even longer if required. Infusion may be carried out at suitable intervals of say 1 to 4 weeks.

The correct dosage of the compounds will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compounds and compositions of the invention may be used with other drugs to provide a combination therapy. The other drugs may form part of the same composition, or be provided as a separate composition for administration at the same time or at different time.

EXAMPLES OF THE INVENTION

Example 1

Production of IB-01211

Inoculum development: a frozen culture of ES7-008 or a well grown slant culture (5% vol.) is used to seed 100 ml of a seed medium, as described in Table 1, that it is contained in a 250 ml shake flask. The flask is incubated during 48 h. A 2 l Erlenmeyer flask with 500 ml of the same medium is seeded with 10% vol. of the first stage inoculum. The flask is incubated during 48 h.

Fermentation step: 50 l of production medium, as described in Table 1, contained in a 75 l fermentation tank are seeded with 2.5 l of second stage inoculum. The fermentation is carried out during 96 h with 400 rpm agitation and an air flow of 0.5V/V.M.

Example 2

Isolation of IB-01211

8.5 liters of whole harvested broth were filtrated to separate the biomass and other solids. The mycelia cake was extracted twice with a mixture solvent (2.4 l) of $CHCl_3:CH_3OH:H_2O$ (2:1:1). The activity was concentrated in the lower layer. The organic solvent was concentrated and evaporated to dryness in vacuo to yield 4.8 g of crude extract.

The extract was applied to a silica gel VFC (vacuum flash chromatography) system, using a mixture of n-hexane-EtOAc and EtOAc-MeOH as eluting solvents. The fractions with antitumour activity, containing IB-01211 (900 mg) were eluted with EtOAc-MeOH 1:1, EtOAc-MeOH 1:3 and methanol. The active fractions were chromatographied twice with a silica gel column using $CHCl_3$-MeOH and EtOAc-MeOH mixtures as eluting solvents. The cytotoxic activity was detected in fractions eluted with $CHCl_3$-MeOH 96:4 in the first chromatography (200 mg of pure compound IB-01211) and in fractions eluted with EtOAc-MeOH 85:15-8:2 in the second chromatography (60 mg of pure compound IB-01211). Further purification with C18 reversed phase chromatography afforded 22 mg of pure compound IB-01211 eluted with MeOH.

Figure 2:
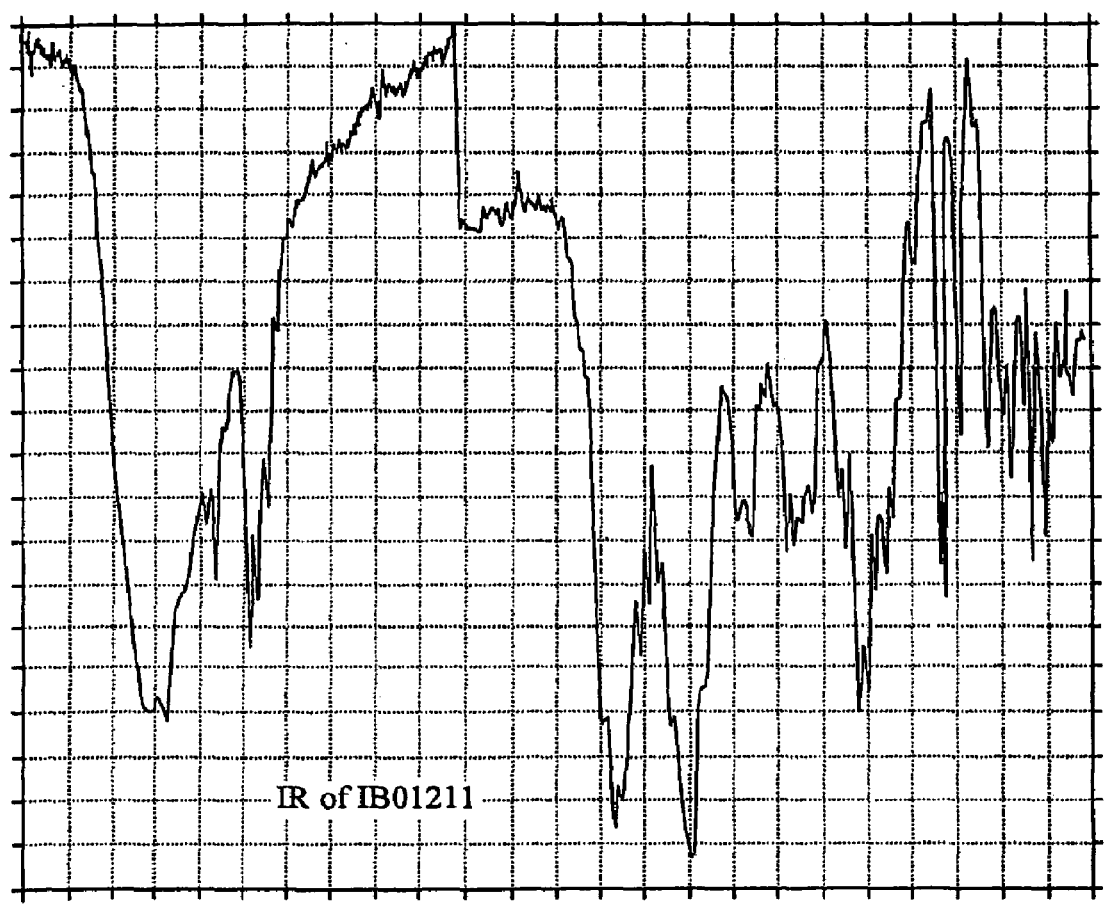
FIG. 2. IR spectrum of purified IB-01211
Figure 3:
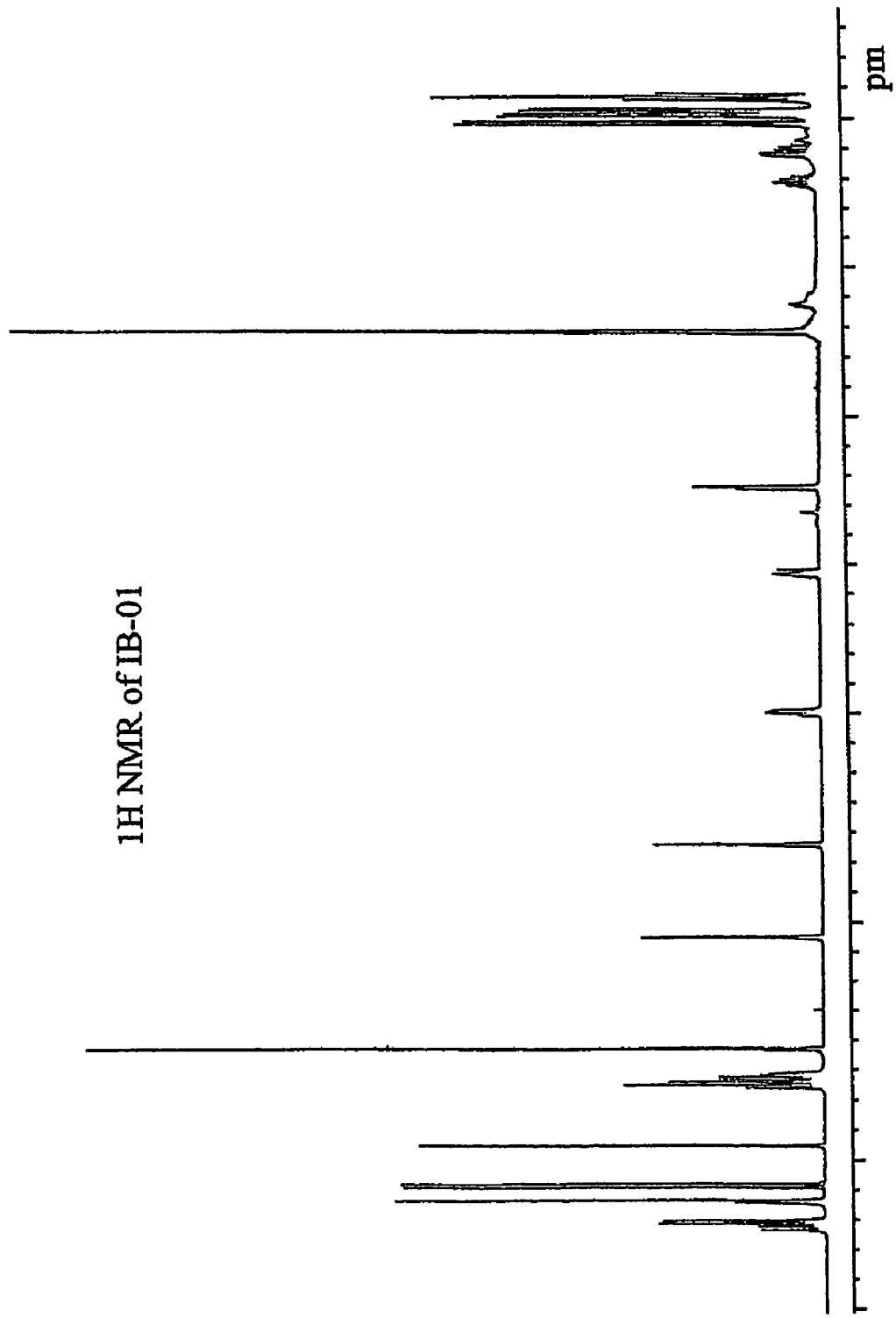
FIG. 3. $^1$H NMR spectrum of purified IB-01211
Figure 4:
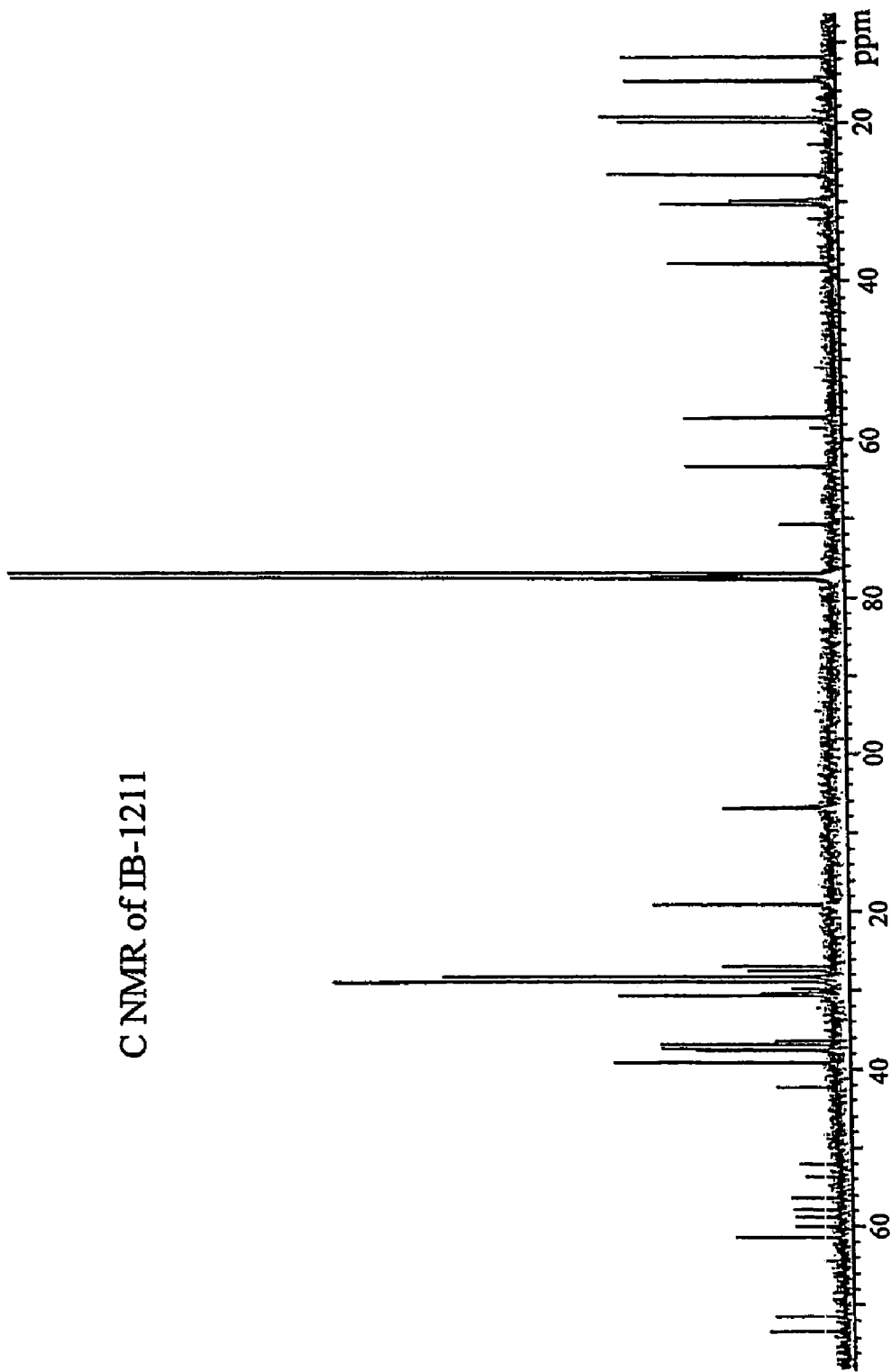
FIG. 4. $^{13}$C NMR spectrum of purified IB-01211
Figure 5:
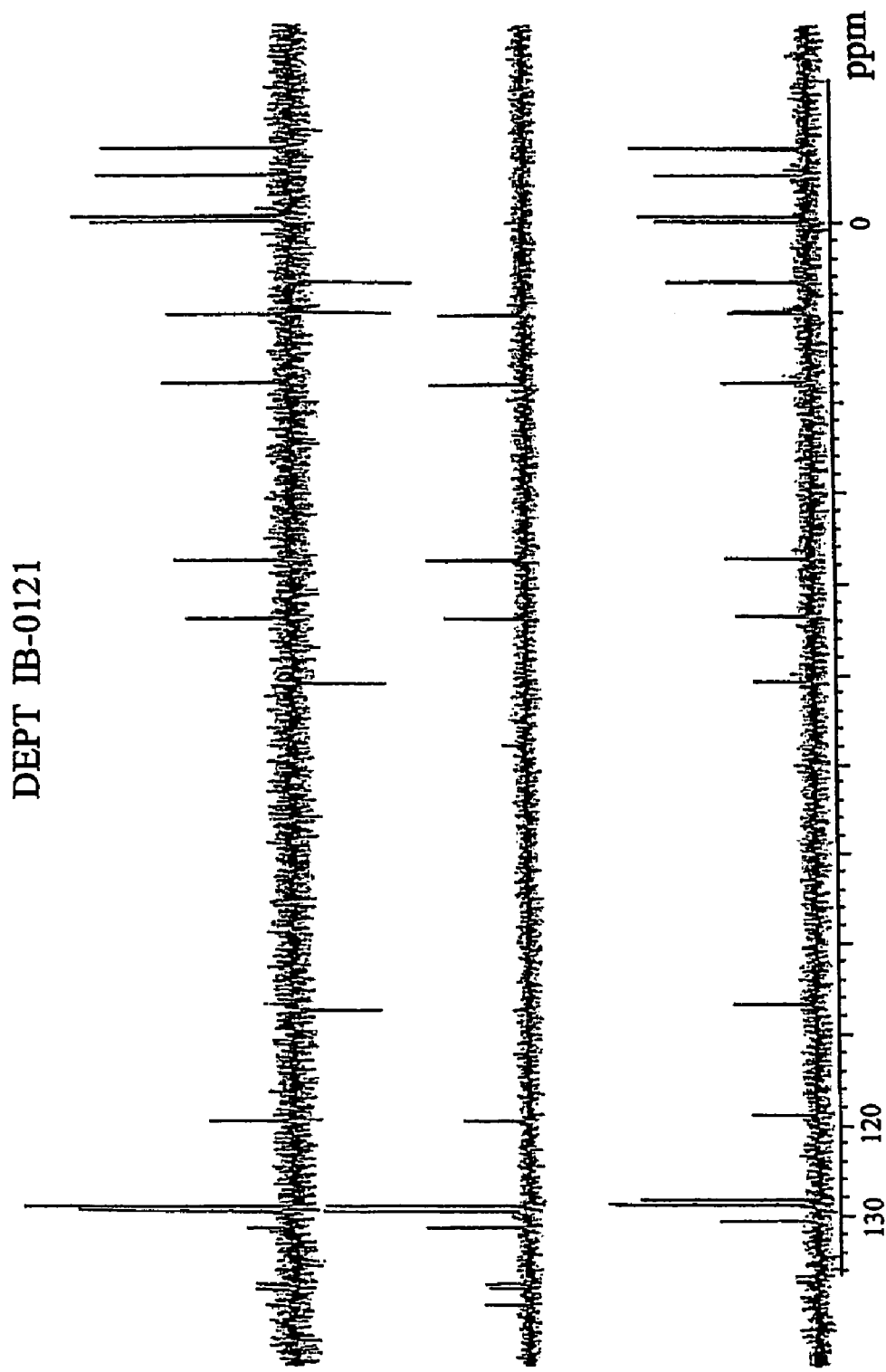
FIG. 5. DEPT spectrum of purified IB-01211
Figure 6:
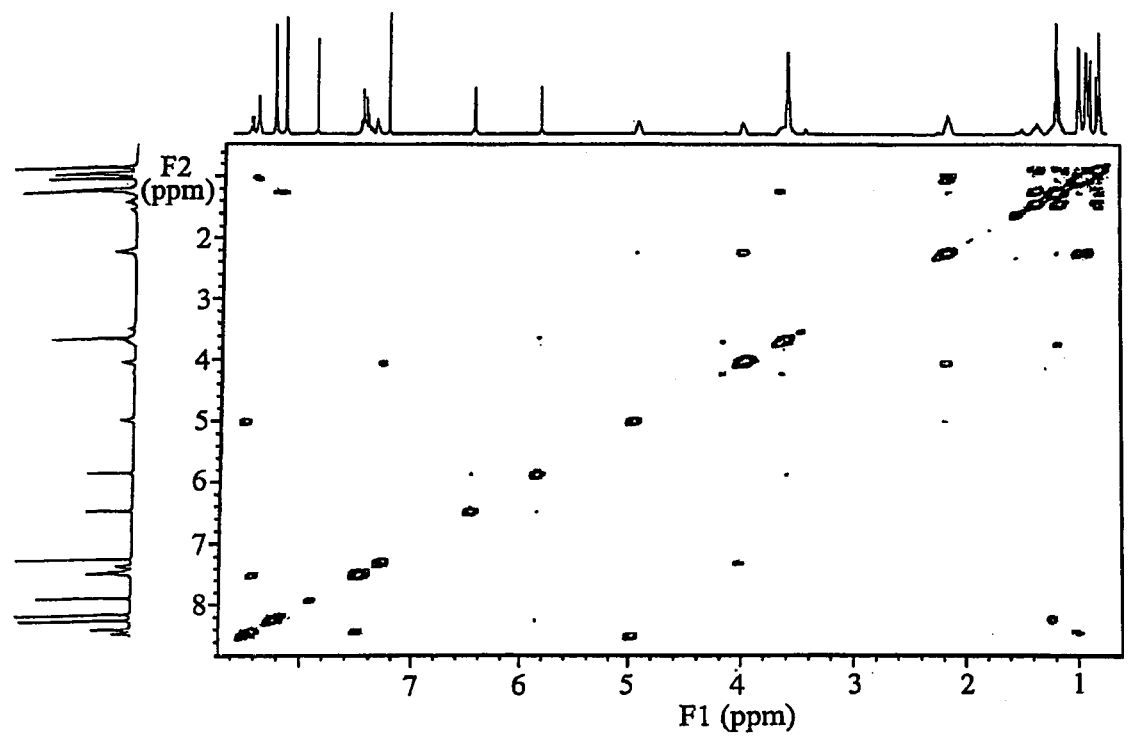
FIG. 6. COSY 45 spectrum of purified IB-01211
Figure 7:
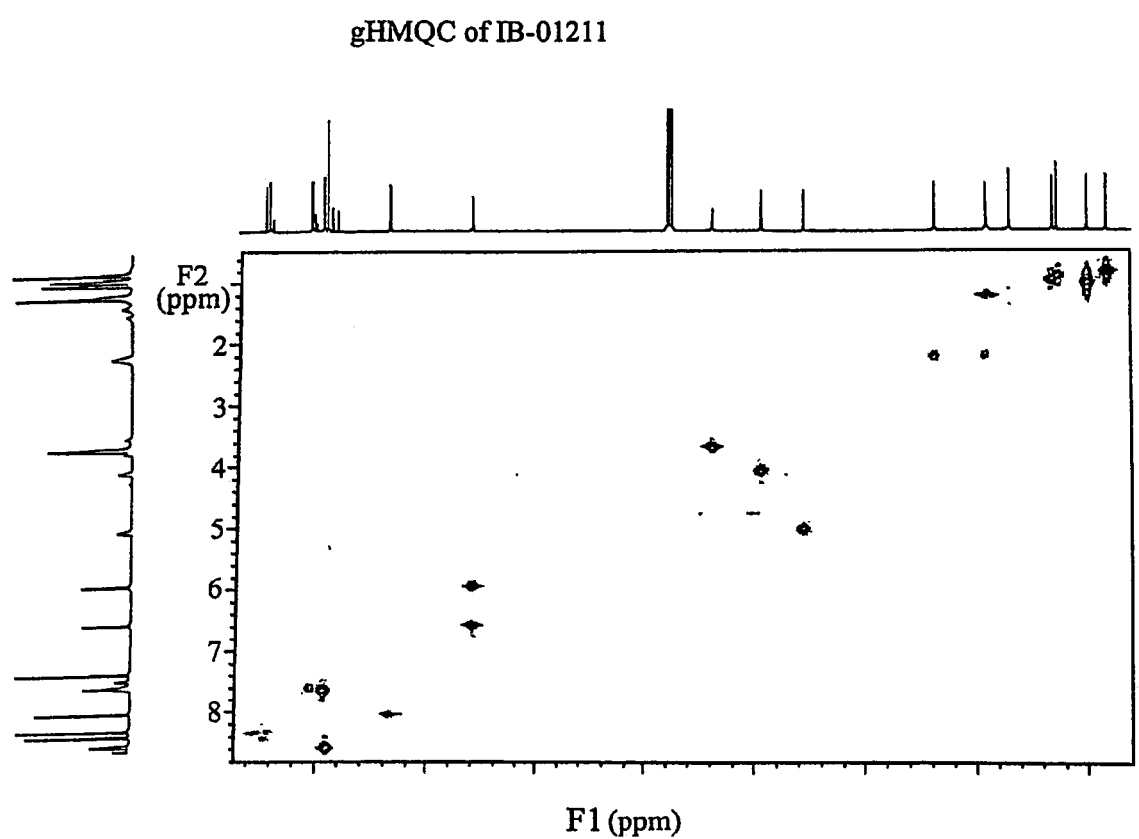
FIG. 7. HMQC spectrum of purified IB-01211
Figure 8:
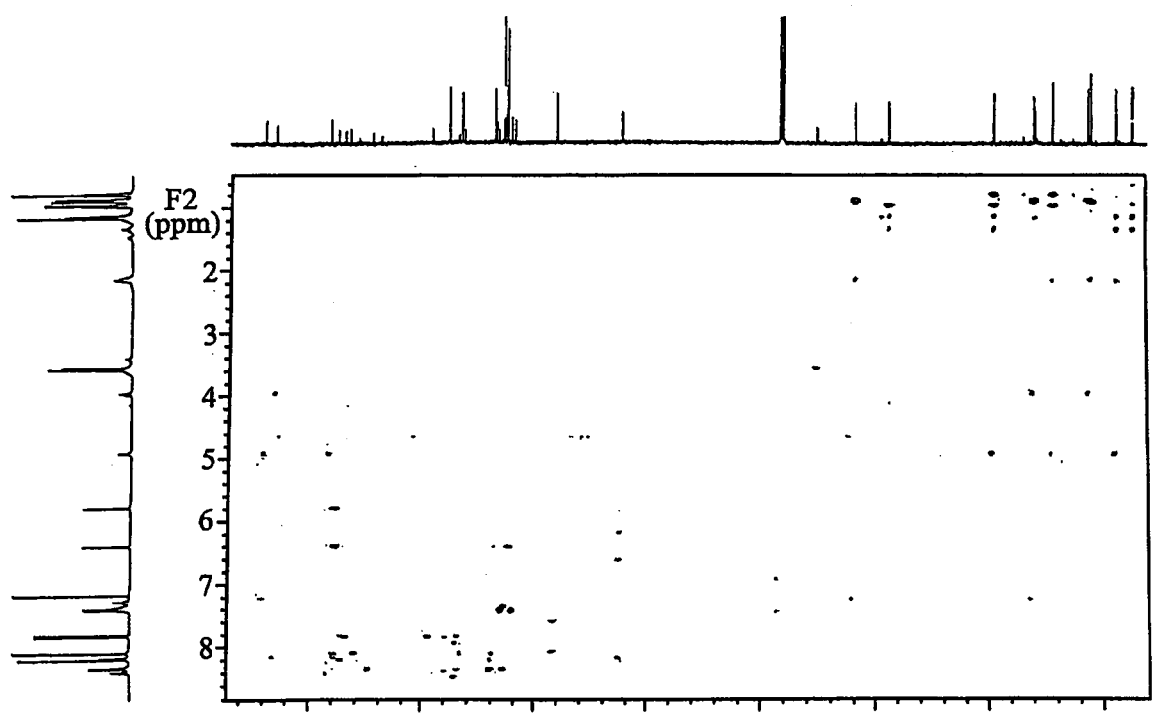
FIG. 8. HMBC spectrum of purified IB-01211

On the basis of detailed analysis of their various spectral characteristics, the pure compound was identified as IB-01211. The UV spectrum shows absorption at 225 nm, 265 nm and 290 nm as reported in FIG. 1. The infrared absorption spectrum is shown in FIG. 2 of the accompanying drawings. The $^1H$ NMR, $^{13}C$ NMR and DEPT spectra of IB-01211 are reported in FIG. 3, FIG. 4 and FIG. 5, respectively. The 2D NMR experiments COSY, HMQC and HMBC are reported in FIG. 6, FIG. 7 and FIG. 8, respectively. The ES-MS spectrum of IB-01211 displays a (M+Na) peak at 731 as reported in FIG. 9. $^1H$ and $^{13}C$ NMR data of compound IB-01211 are summarized in the following table.

| Position | $^{13}C$ (δ) | $^1H$ (δ) |
|---|---|---|
| Isoleucine | | |
| NH | | 8.46(d, 10.6) |
| αCH | 57.3 | 4.99(dd, 10.5, 4.4) |
| βCH | 37.8 | 2.23(m) |
| γCH$_2$ | 26.6 | 1.41(q, 7.5) 1.20(m) |
| γCH$_3$ | 14.9 | 1.05(d, 6.9)) |
| δCH$_3$ | 11.9 | 0.87(t, 7.2) |
| CO | 173.3 | |
| Valine | | |
| NH | | 7.37(d, 5.4) |
| αCH | 63.6 | 4.06(dd, 8.7, 5.6) |
| βCH | 30.2 | 2.21(m) |
| γCH$_3$ | 19.5 | 0.95(d, 6.8) |
| γCH$_3$ | 20.0 | 0.99(d, 6.8) |
| CO | 171.2 | |
| Oxazole (1) | | |
| NH | | 8.28(bs) |
| αC | 127.5 | |
| βCH$_2$ | 106.8 | 6.50(s) |
| | | 5.88(s) |
| 2-C | 159.9 | |
| 4-C | 130.3 | |
| 5-CH | 139.1 | 8.2(s) |
| Oxazole (2) | | |
| 2-C | 156.1 | |
| 4-C | 136.4 | |
| 5-CH | 136.9 | 8.16(s) |
| Thiazole | | |
| 2-C | 157.8 | |
| 4-C | 142.2 | |
| 5-CH | 119.1 | 7.90(s) |
| Oxazole (3) | | |
| 2-C | 158.6 | |
| 4-C | 130.6 | |
| 5-CH | 137.4 | 8.27(s) |
| Oxazole (4) | | |
| 2-C | 152.0 | |
| 4-C | 129.8 | |
| 5-C | 153.6 | |
| 1'-C | 126.8 | |
| 2',6'-CH | 128.3 | 8.42(dd, 7.0, 1.2) |
| 3',5'-CH | 128.8 | 7.49(m) |
| 4'-CH | 130.7 | 7.47(m) |
| CO | 161.2 | |

Example 3

Biological in Vitro Activity

Bioassays for Antitumour Screening

The finality of these assays is to interrupt the growth of an "in vitro" tumour cell culture by means a continued exhibition of the cells to the sample to be testing. The following human cell lines were used:

CELL LINES

| Name | N° ATCC | Tissue | Characteristics |
|---|---|---|---|
| K-562 | CCL-243 | leukemia | erythroleukemia (pleural effusion) |
| A-549 | CCL-185 | lung | lung carcinoma "NSCL" |
| SK-MEL-28 | HTB-72 | melanoma | malignant melanoma |
| HT-29 | HTB-38 | colon | colon adenocarcinoma |
| DU-145 | HTB-81 | prostate | prostate carcinoma, not androgen receptors |
| LNCaP | CRL-1740 | prostate | prostate adenocarcinoma, with androgen receptors |
| PC-3 | CRL-1435 | prostate | prostate adenocarcinoma |
| BT-474 | HTB-20 | breast | breast adenocarcinoma |
| MX-1 |  | breast | breast adenocarcinoma, |
| Hs746t | HTB-135 | gastric | stomach carcinoma |
| SK-HEP-1 | HTB-52 | liver | liver adenocarcinoma |
| SK-OV-3 | HTB-77 | ovary | ovary adenocarcinoma (malignant ascites) |
| PANC-1 | CRL-1469 | pancreas | pancreatic epitheloid carcinoma |
| 5637 | HTB-9 | bladder | bladder carcinoma |
| FADU | HTB-43 | pharynx | squamous cell carcinoma |
| 786-O | CRL-1932 | renal | primary renal cell adenocarcinoma |
| NCI-H187 |  | SCL |  |
| Y-79 | HTB-18 | retinoblastoma | retinoblastoma |
| SW694 | HTB-91 | fibrosarcoma | fibrosarcoma |
| CHSA |  | chondrosarcoma | chondrosarcoma |
| OSA-FH |  | osteosarcoma | osteosarcoma |
| SK-N-MC | HTB-10 | neuroblastoma | neuroepithelioma |
| TT | CRL-1803 | thyroid | medullary thyroid carcinoma |
| SW-579 | HTB-107 | thyroid | thyroid carcinoma |
| HL-60 | CCL-240 | promyelocytic | leukemia |
| H9 | HTB-176 | lymphoma | T-cell-lymphoma |
| MC116 | CRL-1649 | lymphoma | lymphoma |

Inhibition of cell Growth by Counting Cells

Tetrazolium Assay MTS is based on metabolic reduction of MTS to solubilized formazan crystals by the metabolically active mitochondria of living cells. For this reason, the methodology includes counting of the cell lines based on viability staining to ensure that cell concentrations are corrected to allow for 100% living cells into each well in lieu of Coulter counting or estimated dilutions based on standard growth curves.

Medium containing drug was removed at the end of the treatment and culture plates rinsed one time with PBS. Afterward, cells were incubated in 200 µl of drug-free medium until 72 hours. After appropriate incubation time 25 µl of MTS+PMS solution was added to each microtiter well and incubated for 4 hours at 37° C. Plates were then removed from the incubator and placed on plate shaker for 5 minutes (covered for protection from light). Optical densities were read at 490 nm on spectrophotometer plate reader. Data was analyzed using Softmax.

Data is presented as $IC_{50}$ potencies calculated from $3^{rd}$ order polynomial regression curves using Microsoft Excel and then manually interpolated.

The following table illustrates data on the biological activity of the compounds of the present invention.

| Cytotoxic activity (mol/l) of IB-01211 | | |
|---|---|---|
| Bladder | 5637 | 3.39E−7 |
| Breast | BT-474 | 5.37E−7 |
| Breast | MX-1 | 8.62E−7 |
| Colon | HT-29 | 8.17E−7 |
| Gastric | Hs746t | 6.92E−7 |
| Liver | SK-HEP-1 | 6.64E−7 |
| NSCL | A549 | 9.18E−7 |
| Ovary | SK-OV-3 | 9.46E−7 |
| Pancreas | PANC-1 | 4.24E−7 |
| Pharynx | FADU | 6.64E−7 |
| Renal | 786-O | 6.92E−7 |
| Prostate | PC-3 | 6.21E−7 |
| Prostate | DU-145 | 4.8E−7 |
| Prostate | LNCAP | 6.5E−7 |
| SLC | NCI-H187 | 2.97E−8 |
| Retinoblastoma | Y-79 | 9.32E−8 |
| Melanoma | Mel-28 | 5.08E−7 |
| Fibrosarcoma | SW 694 | 7.2E−7 |
| Chondrosarcoma | CHSA | 3.53E−7 |
| Leukemia/Lymphoma | HL-60 | 1.41E−7 |
| Leukemia/Lymphoma | K562 | 6.36E−7 |
| Leukemia/Lymphoma | H9 | 1.84E−7 |
| Leukemia/Lymphoma | MC116 | 3.39E−6 |
| Osteosarcoma | OSA-FH | 7.2E−7 |
| Neuroblastoma | SK-N-MC | 5.37E−7 |
| Thyroid | TT | 4.38E−6 |
| Thyroid | SW-579 | 4.52E−7 |

Example 4

Biological in Vivo Activity

In Vivo Analysis of IB-01211 in Human Breast, Colon and Non-Small Cell Lung Tumour Xenografts Tumour Implantation At different times, three human tumour cell lines MX-1 (breast), HT-29 (colon), and LX-1 (non-small cell lung), respectively, were implanted subcutaneously into separate groups of recipient female athymic mice as a small seedling of approximately 2-3 mm$^3$. Each tumour type was then allowed to grow inside the animal to reach a group mean size of 100±15 mm$^3$, at which time tumour-bearing mice were randomized into groups (Staging Day). The Staging Day also coincided with Day 0 for drug dosing.

Frequency and Route of Administration of the Test Article

The test article was administered as a single intravenous (iv) bolus injection (i.e., QD×1) on the Staging Day (Day 0).

Tumour Measurements

Tumour burden was determined for all animals throughout the study using a caliper, and the frequency was at least twice per week.

Data Analysis

Protocols and criteria for drug activity were derived from those established by the National Cancer Institute for tumour systems similar to those used in these studies (NIH Publication No. 84-2635, In vivo cancer models 1976-1982). Statistical analysis of tumour volumes for each group of drug treated animals was performed according to the Mann Whitney nonparametric test based on comparisons to the vehicle control cohort within the same experiment.

Tumour lengths (L) and widths (W) were measured in millimeters (mm) using calipers, recorded, and tumour volume was calculated by the formula: Volume (mm$^3$)=L×W$^2$×0.5. Individual values were determined for each tumour-bearing athymic- mouse and specified day of measurement (day D). On the tumour Staging Day (Day 0), the tumour volume of a treated animal ($T_0$1) was subtracted from the corresponding tumour volume on each observation day ($T_D$1). This provided the change (Δ) in tumour volume for the said treated athymic mouse (ΔT1=$T_D$1−$T_0$1). The change in tumour volumes for each member of the control cohort (ΔC) was calculated in a similar fashion as above.

Results from tumour xenografts are tabulated below. At randomization (Day 0) the average volume of the tumour mass was 100±15 mm$^3$ and the "net tumour growth" is really a difference between the size of the tumour on Day X and that on Day 0. The parameter S.E.M. is commonly used in statistics and stands for standard error of the mean in a distribution of N (size) experimental values.

Kinetics of net tumour growth after in vivo administration of IB01211 in human breast tumour (MX-1 cell line) xenografts.

| TEST ARTICLE | SINGLE DOSE (mg/kg) | DAY 3 | | DAY 6 | | DAY 10 | |
|---|---|---|---|---|---|---|---|
| | | Net Tumour Growth ± S.E.M. (mm$^3$) | P Value* | Net Tumour Growth ± S.E.M. (mm$^3$) | P Value* | Net Tumour Growth ± S.E.M. (mm$^3$) | P Value* |
| Vehicle Control | — | 124 ± 30 | — | 252 ± 20 | — | 780 ± 129 | — |
| IB-01211 | 1.0 | 5 ± 3 | 0.0952$^§$ | 113 ± 62 | 0.0952$^§$ | 450 ± 137 | 0.3810 |
| | 1.5 | † | — | † | — | † | — |

*P < 0.05, statistically significant (according to the Mann Whitney nonparametric test: given group compared to the Vehicle Control cohort).
$^§$P > 0.05 but <0.096, trend to statistical significance.
† High mortality prevented meaningful statistical analysis.

Kinetics of net tumour growth after in vivo administration of IB01211 in human colon tumour (HT-29 cell line) xenografts.

| TEST ARTICLE | SINGLE DOSE (mg/kg) | DAY 1 | | DAY 4 | | DAY 8 | |
|---|---|---|---|---|---|---|---|
| | | Net Tumour Growth ± S.E.M. (mm$^3$) | P Value* | Net Tumour Growth ± S.E.M. (mm$^3$) | P Value* | Net Tumour Growth ± S.E.M. (mm$^3$) | P Value* |
| Vehicle Control | — | 7 ± 10 | — | 46 ± 14 | — | 126 ± 32 | — |
| IB01211 | 0.5 | 26 ± 11 | 0.3095 | 53 ± 28 | 0.6905 | 162 ± 34 | 0.8413 |

*P < 0.05, statistically significant (according to the Mann Whitney nonparametric test: given group compared to the Vehicle Control cohort).
N.T., not tested.

Kinetics of net tumour growth after in vivo administration of IB01211 in human non-small cell lung tumour (LX-1 cell line) xenografts.

| TEST ARTICLE | SINGLE DOSE (mg/kg) | DAY 3 | | DAY 6 | | DAY 10 | |
|---|---|---|---|---|---|---|---|
| | | Net Tumour Growth ± S.E.M. (mm$^3$) | P Value* | Net Tumour Growth ± S.E.M. (mm$^3$) | P Value* | Net Tumour Growth ± S.E.M. (mm$^3$) | P Value* |
| Vehicle Control | — | 166 ± 30 | — | 307 ± 85 | — | 467 ± 77 | — |
| IB01211 | 1.0 | 68 ± 29 | 0.0556§ | 234 ± 11 | 0.6905 | 561 ± 60 | 0.2222 |
| | 1.5 | 11 ± 19 | 0.0079* | 121 ± 51 | 0.0556§ | 309 ± 71 | 0.2222 |

*P < 0.05, statistically significant (according to the Mann Whitney nonparametric test: given group compared to the Vehicle Control cohort).
§P > 0.05 but <0.06, trend to statistical significance.

In conclusion, the compound IB01211, with a corresponding maximum tolerated dose (MTD) of 3.5 mg/kg in conventional CD-1 mice, demonstrated significant antitumour effect in vivo against a human non-small cell lung tumour at a dose of 0.43 MTD, and showed a trend to significance against breast tumour at a dose of 0.29 MTD, but not against colon tumour at a dose of 0.14 MTD.

The invention claimed is:

1. A purified compound of general formula I:

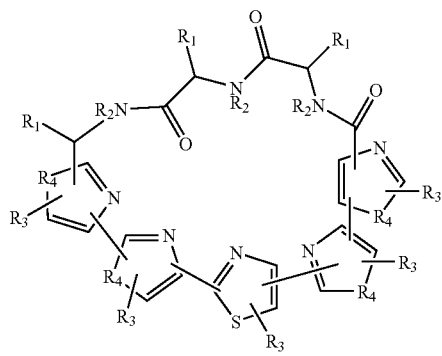

(I)

wherein $R_1$ are each independently selected from the group consisting of hydrogen, halogen, cyano, hydroxyl, nitro, azido, substituted or unsubstituted alkyl, substituted or unsubstituted alkylidene, substituted or unsubstituted alkenyl, substituted or unsubstituted alkynyl, substituted or unsubstituted alkoxy, substituted or unsubstituted aryl, substituted or unsubstituted heterocyclic group and substituted or unsubstituted acyl; $R_3$ groups are each independently selected from the group consisting of hydrogen, halogen, cyano, hydroxyl, nitro, azido, substituted or unsubstituted alkyl, substituted or unsubstituted alkenyl, substituted or unsubstituted alkynyl, substituted or unsubstituted alkoxy, substituted or unsubstituted aryl, substituted or unsubstituted heterocyclic group and substituted or unsubstituted acyl $R_4$ groups are each independently selected from $NR_2$, O and S; and $R_2$ groups are each independently selected from the group consisting of hydrogen, substituted or unsubstituted alkyl, substituted or unsubstituted aryl, substituted or unsubstituted alkoxy and substituted or unsubstituted acyl, or a pharmaceutically acceptable salt, derivative, prodrug or stereoisomer thereof.

2. The compound according to claim 1, having the following formula II:

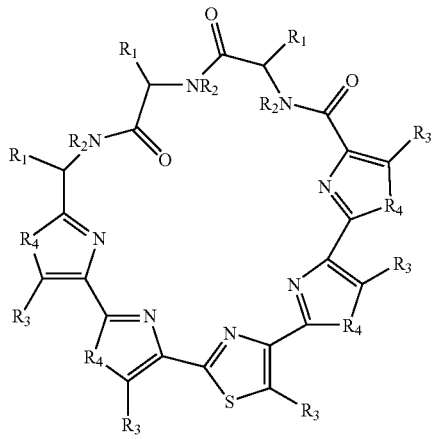

(II)

wherein $R_1$, $R_2$, $R_3$ and $R_4$ are as defined in claim 1.

3. The compound according to claim 1, wherein $R_1$ are each independently selected from substituted or unsubstituted alkyl and substituted or unsubstituted alkylidene.

4. The compound according to claim 1, wherein $R_2$ are each independently selected from H and substituted or unsubstituted alkyl.

5. The compound according to claim 1, wherein $R_3$ are each independently selected from H and substituted or unsubstituted aryl.

6. The compound according to claim 1, wherein $R_4$ are each O.

7. The compound according to claim 1, having the following formula

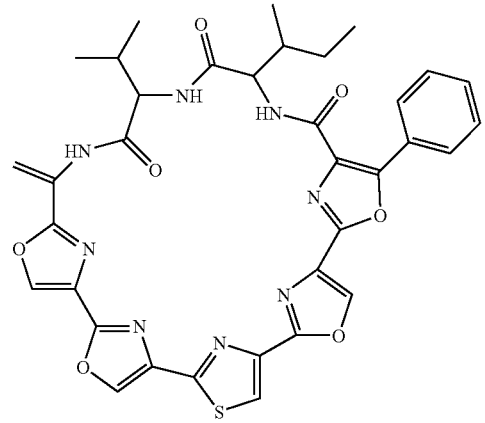

or a pharmaceutically acceptable salt, derivative, prodrug or stereoisomer thereof.

8. The compound according to claim 7, having the following stereochemistry

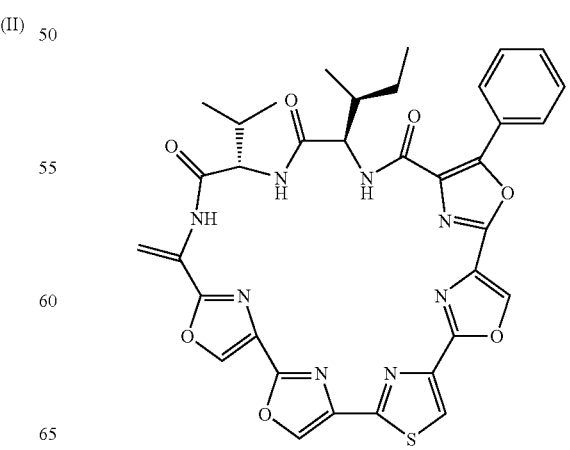

9. A process for producing a compound as defined in claim 1 which comprises synthesising a oxazole/thiazole/imidazole fragment, and introducing an aminoacidic fragment.

10. A process for preparing a compound as defined in claim 7 which comprises (i) cultivating a substantially pure culture strain ES7-008, available under accession number CECT 3358, from the Colección Espanola de Cultivos Tipo at the University of Valencia, Spain (ii) isolating said compound from the cultured broth.

11. A pharmaceutical composition comprising a compound as defined in claim 1, or a pharmaceutically acceptable salt, derivative, prodrug or stereoisomer thereof and a pharmaceutically acceptable diluent or carrier.

12. A method of treatment of cancer which comprises administering an effective amount of a compound as defined in claim 1, or a pharmaceutically acceptable salt, derivative, prodrug or stereoisomer thereof.

13. The process of claim 10, wherein the cultivating is performed in an aqueous nutrient medium with assimilable carbon and nitrogen sources and salts.

* * * * *